(12) United States Patent
Arhancet et al.

(10) Patent No.: US 9,902,690 B2
(45) Date of Patent: Feb. 27, 2018

(54) ETHOXYLATED SURFACTANTS

(71) Applicants: Novus International Inc., St. Charles, MO (US); Board of Regents of the University of Oklahoma, Norman, OK (US)

(72) Inventors: Graciela Arhancet, St. Charles, MO (US); Scott Long, St. Charles, MO (US); Xiaojun Wang, St. Charles, MO (US); Richard Vonder Embse, St. Charles, MO (US); Brian Grady, Norman, OK (US); Jeff Harwell, Norman, OK (US); Guangzhe Yu, Norman, OK (US)

(73) Assignees: Novus International, Inc., St. Charles, MO (US); Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/107,226

(22) PCT Filed: Dec. 22, 2014

(86) PCT No.: PCT/US2014/071860
§ 371 (c)(1),
(2) Date: Jun. 22, 2016

(87) PCT Pub. No.: WO2015/100225
PCT Pub. Date: Jul. 2, 2015

(65) Prior Publication Data
US 2016/0340302 A1   Nov. 24, 2016

Related U.S. Application Data

(60) Provisional application No. 61/921,282, filed on Dec. 27, 2013.

(51) Int. Cl.
| | | |
|---|---|---|
| *A61K 8/46* | (2006.01) | |
| *C07C 317/46* | (2006.01) | |
| *C08G 75/14* | (2006.01) | |
| *C08G 75/18* | (2006.01) | |
| *C11D 1/00* | (2006.01) | |
| *C11D 1/29* | (2006.01) | |
| *C11D 1/755* | (2006.01) | |
| *C11D 11/00* | (2006.01) | |
| *C11D 3/22* | (2006.01) | |
| *C11D 3/37* | (2006.01) | |
| *A61Q 19/00* | (2006.01) | |

(52) U.S. Cl.
CPC ............ *C07C 317/46* (2013.01); *A61K 8/46* (2013.01); *A61Q 19/00* (2013.01); *C08G 75/14* (2013.01); *C08G 75/18* (2013.01); *C11D 1/29* (2013.01); *C11D 3/22* (2013.01); *C11D 3/3715* (2013.01); *C11D 3/3719* (2013.01); *C11D 11/0017* (2013.01)

(58) Field of Classification Search
CPC ......... C11D 1/29; C11D 11/0017; C11D 3/22; C11D 3/3715; C11D 3/3719; C11D 317/46; C11D 1/008; C11D 1/755; C08G 75/14; C08G 75/18; A61K 8/46; A61Q 19/00; C07C 317/46
See application file for complete search history.

(56) References Cited

U.S. PATENT DOCUMENTS

| | | | |
|---|---|---|---|
| 4,464,292 | A | 8/1984 | Lengyel |
| 4,749,811 | A | 6/1988 | Cesa |
| 4,794,187 | A | 12/1988 | Glossmann |
| 4,808,622 | A | 2/1989 | Kinast et al. |
| 5,061,710 | A | 10/1991 | Haslanger |
| 6,358,978 | B1 | 3/2002 | Ritzeler et al. |
| 7,316,996 | B2 * | 1/2008 | Muhlradt ......... A61K 47/48215 514/1.4 |
| 8,053,194 | B2 | 11/2011 | Kazuo |
| 9,169,203 | B2 | 10/2015 | Grady |
| 2002/0077306 | A1 | 6/2002 | Dinkelborg |
| 2010/0252433 | A1 | 10/2010 | Dratz |
| 2011/0262492 | A1 | 10/2011 | Messersmith |
| 2013/0178540 | A1 * | 7/2013 | Grady .................... C11D 1/002 514/785 |

FOREIGN PATENT DOCUMENTS

| | | |
|---|---|---|
| DE | 3600593 A1 | 7/1987 |
| DE | 3600594 A1 | 7/1987 |
| EP | 322633 A1 | 7/1989 |
| EP | 1382352 | 1/2004 |
| WO | 9300908 A1 | 1/1993 |
| WO | 9534535 A1 | 12/1995 |
| WO | 9812156 A1 | 3/1998 |

(Continued)

OTHER PUBLICATIONS

CAS No. 1306322-34-8, Entered in STN Jun. 6, 2011, p. 1.*
Braunova et al. "Hydrolytically and Reductively Degradable High-Molecular-Weight Poly(ethylene glycol)s," Macromolecular Chemistry and Physics (2007), 208(24), 2642-2653.
Crich et al., "Amino Acid and Peptide Synthesis and Functionalization by the Reaction of Thioacids with 2,4-Dinitrobenzenesulfonamides," Organic Letters (2007), 9(22), 4423-4426.
Hamachi et al. "Anisotropic incorporation of lipid-anchored myoglobin into a phospholipid bilayer membrane," J. Am. Chem. Soc., 1993, 115(12), 4966-4970.
Hooks et al. "Development of homomultimers and heteromultimers of lung cancer-specific peptoids," Biopolymers, 2011, 96(5), 567-577.

(Continued)

*Primary Examiner* — Pancham Bakshi
*Assistant Examiner* — Mark R Luderer
(74) *Attorney, Agent, or Firm* — Polsinelli PC

(57) ABSTRACT

The present invention provides sulfur- or selenium-containing compounds comprising hydrophobic moieties and ethoxylated ester or ethoxylated amide moieties such that the compounds have surfactant properties. Also provided are methods for using the disclosed compounds or mixtures thereof in a variety of applications.

27 Claims, No Drawings

(56) References Cited

FOREIGN PATENT DOCUMENTS

| | | | |
|---|---|---|---|
| WO | 9506484 | A1 | 8/1998 |
| WO | 2001000610 | A1 | 6/1999 |
| WO | 2000061537 | A2 | 10/2000 |
| WO | 2005011738 | A2 | 2/2005 |
| WO | 2005042546 | A2 | 5/2005 |
| WO | 2005094187 | A1 | 10/2005 |
| WO | 2006057868 | A1 | 6/2006 |
| WO | 2007030012 | A2 | 3/2007 |
| WO | 2007092847 | A2 | 8/2007 |
| WO | 2007136703 | A1 | 11/2007 |
| WO | 2009005871 | A2 | 1/2009 |
| WO | 2009055054 | A2 | 4/2009 |
| WO | 2009055653 | A1 | 4/2009 |
| WO | 2010013138 | A2 | 2/2010 |
| WO | 2010033223 | A1 | 3/2010 |
| WO | 2008114505 | A1 | 7/2010 |
| WO | 2010128303 | A1 | 11/2010 |
| WO | 2011008985 | A2 | 1/2011 |
| WO | 2011046946 | A2 | 4/2011 |
| WO | 2011119759 | A1 | 9/2011 |
| WO | 2012006475 | A1 | 1/2012 |
| WO | 2013059107 | A1 | 4/2013 |
| WO | 2015100225 | A1 | 7/2015 |

OTHER PUBLICATIONS

Itoh et al., "Design, synthesis, structure—selectivity relationship, and effect on human cancer cells of a novel series of histone deacetylase 6-selective inhibitors," Journal of Medicinal Chemistry (2007), 50(22), 5425-5438.
Joullie et al. "Evolution of amide bond formation," ARKIVOC 2010 (viii) 189-250.
Katritzky et al., "Convenient and Efficient Preparation of N-Protected ($\alpha$-Aminoacyl)oxy-Substituted Terpenes and Alkanes," Synthesis (2006), (24), 4135-4142.
Landis et al., "Solid-phase synthesis of chiral 3,4-diazaphospholanes and their application to catalytic asymmetric allylic alkylation," Proceedings of the National Academy of Sciences of the United States of America (2004), 101(15), 5428-5432.
Liu et al. "Synthesis and insecticidal activities of novel spin-labeled derivatives of camptothecin," Heteroatom Chemistry (2011), 22(6), 687-691.
Liu et al., "Chemistry of Periodate-Mediated Cross-Linking of 3,4-Dihydroxylphenylalanine-Containing Molecules to Proteins," Journal of the American Chemical Society (2006), 128(47), 15228-15235.
Montalbetti et al. "Amide bond formation and peptide coupling," Tetrahedron, 2005, 61, 10827-10852.
Rahman et al. "Conformation and biological studies of synthesized Trp4-Met5 enkephalin N-protected with 3,5-dimethoxy-alpha,alpha-dimethylbenzoylcarbonyl group," Die Pharmazie (1988), 43(2), 116-17.
Rahman et al., "Relationship between conformation and physicochemical properties of polypeptides. I. Synthesis of homo- and co-oligopeptides by the liquid-phase method," Biopolymers (1980), 19(1), 173-17.
Ribeiro et al., "1H-nmr studies of polyoxyethylene-bound homo-oligo-L-methionines," Biopolymers (1982), 21(11), 2225-2239.
Valeur et al. "Amide bond formation: beyond the myth of coupling reagents," Chem. Soc. Rev. 2009, 38, 606-631.
International Search Report and Written Opinion dated Mar. 26, 2015 from related International application No. PCT/US14/71860, 9 pgs.
Office action dated Jan. 25, 2017 from related Chinese application No. 201480071316.8, 20 pgs.
STN International registry online search record dated Nov. 13, 2011, 3 pgs.

* cited by examiner

ETHOXYLATED SURFACTANTS

CROSS-REFERENCE TO RELATED APPLICATIONS

This application is a U.S. National Stage Application of PCT International Application No. PCT/US2014/071860, filed Dec. 22, 2014, which claims priority to U.S. Provisional Application Ser. No. 61/921,282, filed Dec. 27, 2013, the disclosure of each is hereby incorporated by reference in its entirety.

FIELD OF THE INVENTION

The present disclosure generally relates to surfactants. In particular, it relates to sulfur- or selenium-containing compounds comprising hydrophobic moieties and ethoxylated ester or amide moieties such that the compounds have surfactant properties.

BACKGROUND OF THE INVENTION

Surfactants (or surface active agents) are compounds that lower the surface tension of a liquid, the interfacial tension between two liquids, or the interfacial tension between a liquid and a solid. Surfactants function as cleaning, wetting, dispersing, emulsifying, foaming, and anti-foaming agents in numerous practical applications and products. Accordingly, surfactants are present in detergents and other cleaning products, cosmetics, and are used in a wide variety of industrial processes.

Because of the wide use of surfactants, there is a need for surfactants that are rapidly biodegradable, nontoxic, hard water tolerant, and do not precipitate or gel over a wide range of concentrations and temperatures.

SUMMARY OF THE INVENTION

Among the various aspects of the present disclosure is the provision of a compound comprising Formula (I):

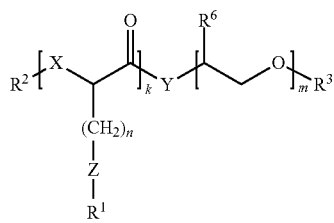

(I)

wherein:
$R^1$ is hydrocarbyl or substituted hydrocarbyl;
$R^2$ is hydrogen, hydrocarbyl, or substituted hydrocarbyl;
$R^3$ is alkyl or alkenyl having 3 or more carbon atoms;
$R^6$ is hydrogen or alkyl;
X and Y independently are O or NH;
Z is sulfur, sulfoxide, sulfone, or selenium; and
k, n, and m independently are integers of 1 or greater.

Another aspect of the present disclosure encompasses a method for cleaning an article. The methods comprises contacting the article with a composition comprising at least one compound comprising Formula (I):

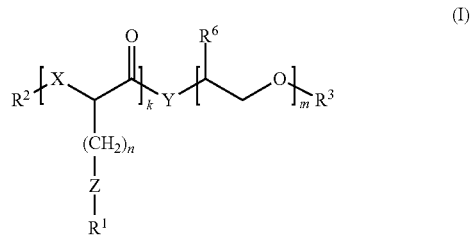

(I)

wherein:
$R^1$ is hydrocarbyl or substituted hydrocarbyl;
$R^2$ is hydrogen, hydrocarbyl, or substituted hydrocarbyl;
$R^3$ is alkyl or alkenyl having 3 or more carbon atoms;
$R^6$ is hydrogen or alkyl;
X and Y independently are O or NH;
Z is sulfur, sulfoxide, sulfone, or selenium; and
k, n, and m independently are integers of 1 or greater.

A further aspect of the present disclosure provides a polymer comprising:
a) at least one subunit A having the following structure:

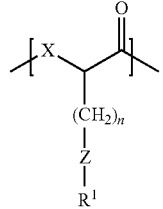

b) at least one subunit B having the following structure:

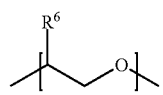

and
c) at least one subunit C, optionally unsaturated, having the following structure:

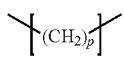

wherein:
$R^1$ is hydrocarbyl or substituted hydrocarbyl;
$R^6$ is hydrogen or alkyl;
X is O or NH;
Z is sulfur, sulfoxide, sulfone, or selenium;
n is an integer of 1 or greater; and
p is an integer of 3 or greater.

Still another aspect of the present disclosure encompasses a method for cleaning an article. The method comprises contacting the article with a composition comprising at least one polymer comprising:

a) at least one subunit A having the following structure:

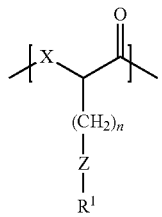

b) at least one subunit B having the following structure:

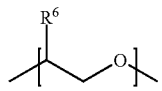

and c) at least one subunit C, optionally unsaturated, having the following structure:

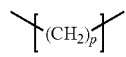

wherein:

$R^1$ is hydrocarbyl or substituted hydrocarbyl;

$R^6$ is hydrogen or alkyl;

X is O or NH;

Z is sulfur, sulfoxide, sulfone, or selenium;

n is an integer of 1 or greater; and p is an integer of 3 or greater.

Other features and iterations of the invention are described in more detail below.

DETAILED DESCRIPTION OF THE INVENTION

The present disclosure provides monomeric or oligomeric sulfide (i.e., thioether), sulfoxide, sulfone, or selenide compounds comprising ethoxylated ester or ethoxylated amide moieties and hydrophobic moieties such that the compounds are interfacially active at oil-water, solid-water, and/or air-water interfaces. The ethoxylated ester or ethoxylated amide moieties provide increased water solubility, and the hydrophobic moieties of the compounds provide oil solubility. Thus, the compounds disclosed herein are oligomeric terpolymers in that they can comprise repeated sulfur/selenium-containing moieties, alkylene oxide repeats, and hydrophobic regions (e.g., methylene repeats).

Advantageously, the surfactant compounds disclosed herein (or mixtures thereof) have critical micelle concentrations in water and are interfacially active at oil-water, solid-water, and/or air-water interfaces. Moreover, the compounds disclosed herein have improved solubility compared to their corresponding ethoxylated alcohols. Accordingly, aqueous solutions containing the surfactant compounds or mixtures thereof have low surface tensions, and excellent tolerance to divalent cations (i.e., hardness tolerance). Consequently, the compounds disclosed herein are useful in many surfactant-containing products and/or applications.

(I) Compounds Comprising Formula (I)

(a) Individual Monomers and Oligomers

One aspect of the present disclosure provide compounds comprising Formula (I):

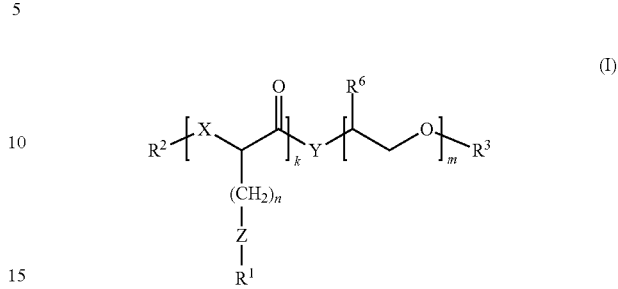

wherein:

$R^1$ is hydrocarbyl or substituted hydrocarbyl;

$R^2$ is hydrogen, hydrocarbyl, or substituted hydrocarbyl;

$R^3$ is alkyl or alkenyl having 3 or more carbon atoms;

$R^6$ is hydrogen or alkyl;

X and Y independently are O or NH;

Z is sulfur, sulfoxide, sulfone, or selenium; and k, n, and m independently are integers of 1 or greater In various embodiments, $R^1$ may be alkyl, alkenyl, alkynyl, aryl, substituted alkyl, substituted alkenyl, substituted alkynyl, or substituted aryl. Additionally, $R^1$ in each repeat unit may differ. In exemplary embodiments, $R^1$ may be $C_1$ to $C_{10}$ alkyl or $C_1$ to $C_6$ alkyl, with the alkyl being linear, branched, or cyclic. In some embodiments, $R^1$ may be methyl, ethyl, propyl, isopropyl, butyl, tert-butyl, hexyl, cyclohexyl, and the like. In specific embodiments, $R^1$ may be methyl.

In certain embodiments, $R^2$ may be hydrogen, alkyl, substituted alkyl, alkenyl, substituted alkenyl, aryl, or substituted aryl. In some embodiments, $R^2$ may be hydrogen, $C_1$ to $C_{10}$ alkyl, phenyl, substituted phenyl, or benzyl. In specific embodiments, $R^2$ may be hydrogen or $C_1$ to $C_6$ alkyl.

In general, $R^3$ is an alkyl or alkenyl chain having 3 or more carbon atoms, wherein the alkyl or alkenyl may be linear or branched. For example, $R^3$ may comprise up to about 500 carbons atoms. In various embodiments, $R^3$ may range from $C_3$ to about $C_{500}$, from $C_3$ to about $C_{400}$, from $C_3$ to about $C_{300}$, from $C_3$ to about $C_{200}$, from $C_3$ to about $C_{100}$, from $C_3$ to about $C_{50}$, or from $C_3$ to about $C_{36}$. In certain embodiments, $R^3$ may range from $C_6$ to $C_{30}$. In other embodiments, $R^3$ may range from $C_8$ to $C_{22}$. For example, $R^3$ may be $C_8$, $C_9$, $C_{10}$, $C_{12}$, $C_{14}$, $C_{16}$, $C_{18}$, $C_{20}$, or $C_{22}$.

In certain embodiments, $R^6$ may be hydrogen or $C_1$ to $C_{10}$, with the alkyl being linear or branched. Additionally, $R^6$ in each repeat unit may differ. In some embodiments, $R^6$ may be $C_1$ to $C_6$ alkyl. In other embodiments, $R^6$ may be hydrogen.

In some embodiments, X may be O and Y may be O. In other embodiments, X may be O and Y may be NH. In still other embodiments, X may be NH and Y may be O. In further embodiments, X may be NH and Y may be NH.

In certain embodiments, Z may be sulfur. In other embodiments, Z may be sulfoxide. In still other embodiments, S may be sulfone. In yet other embodiments, Z may be selenium.

In general, n may range from 1 to about 20 or from 1 to about 10. In some embodiments, n may range from about 1 to about 6. In specific embodiments, n may be 1, 2, 3, or 4.

In various embodiments, k may range from 1 to about 500, from 1 to about 400, from 1 to about 300, from 1 to about 200, from 1 to about 100, from 1 to about 50, from 1 to about 30, from 1 to about 20, from 1 to about 10, or from 1 to about 5. In certain embodiments, k may be 1, 2, 3, 4, 5, 6, 7, 8, 9, 10, 11, 12, 13, 14, 15, 16, 17, 18, 19, or 20.

In general, m may range from 1 to about 500, from 1 to about 400, from 1 to about 300, from 1 to about 200, from 1 to about 100, from 1 to about 50, from 1 to about 30, from 1 to about 20, or from 1 to about 10. In specific embodiments, m may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, $R^1$ may be $C_1$ to $C_{10}$ alkyl, $R^2$ may be hydrogen or $C_1$ to $C_{10}$ alkyl, $R^3$ may be $C_3$ to $C_{200}$, $R^6$ may be hydrogen or $C_1$ to $C_{10}$ alkyl, n may be 1 to 10, k may be 1 to 300, and m may be 1 to 300. In specific embodiments, $R^1$ may be methyl; $R^2$ may be hydrogen; $R^3$ may be $C_6$ to $C_{30}$, $R^6$ may be hydrogen; Z may be sulfur or sulfoxide; X may be O; Y may be O or NH; n may be 2; k may be 1 to 10, and m may be 1 to 30.

(b) Mixtures of Compounds

Also provided herein a mixture of compounds comprising at least two different compounds comprising Formula (I), wherein at least one of $R^1$, $R^2$, $R^3$, $R^6$, X, Y, Z, k, n, or m varies among the different compounds.

In one embodiment, the mixture may comprise compounds in which $R^1$, $R^2$, $R^3$, $R^6$, X, Y, Z, k, and n are the same in every compound, but in which m varies. For example, the mixture may comprise a first set of compounds in which m is 1, a second set of compounds in which m is 2, a third set of compound in which m is 3, a fourth set of compounds in which m is 4, a fifth set of compound in which m is 5, a six set of compound in which m is 6, a seventh set of compound in which m is seven, and so forth.

In another embodiment, the mixture may comprise compounds in which $R^1$, $R^2$, $R^6$, X, Y, Z, k, n, and m are the same in every compound, but in which $R^3$ varies. For example, the mixture may comprise a first set of compounds in which $R^3$ is $C_8$, a second set of compounds in which $R^3$ is $C_{10}$, a third set of compound in which $R^3$ is $C_{12}$, a fourth set of compounds in which $R^3$ is $C_{14}$, a fifth set of compounds in which $R^3$ is $C_{16}$, and the like.

In still another embodiment, the mixture may comprise a set of compounds in which $R^1$, $R^2$, $R^6$, X, Y, Z, k, and n are the same in every compound, but in which both m and $R^3$ vary, as exemplified above.

In a further embodiment, the mixture may comprise a set of compounds in which $R^1$, $R^2$, $R^3$, $R^6$, X, Y, Z, m, and n are the same in every compound, but in which k varies. For example, the mixture may comprise a first set of compound in which k is 1, a second set of compound in which k is 2, a third set of compounds in which k is 3, a fourth set of compounds in which k is 4, a fifth set of compounds in which k is 5, and so forth.

Thus, it should be apparent that any one of $R^1$, $R^2$, $R^3$, $R^6$, X, Y, Z, k, n, or m may vary, or that any combination of $R^1$, $R^2$, $R^3$, $R^6$, X, Y, Z, k, n, and m may vary. For example, in one embodiment, the mixture may comprise compounds in which $R^1$ is methyl, $R^2$ is hydrogen, $R^6$ is hydrogen, X is O; Y is O or NH, Z is sulfur or sulfoxide, n is 2, k ranges from 1 to 10, m ranges from 1 to 30, and $R^3$ ranges from $C_6$ to $C_{30}$.

The amount of each different type of compound in a mixture of compounds can and will vary. For example, the amount of each set of compounds in a mixture may range from about 1% to about 99% of the total weight of the mixture.

(c) Properties of the Compounds or Mixtures of Compounds

In general, the compounds comprising Formula (I) or mixtures of compounds comprising Formula (I) detailed above have a critical micelle concentration (CMC) in water at 25° C. and atmospheric pressure. For example, the CMC of a compound comprising Formula (I) or a mixture of compounds comprising Formula (I) may range from about 0.0001 to about 100 mM in water at 25° C. and atmospheric pressure. In various embodiments, a compound comprising Formula (I) may have a CMC that ranges from about 0.0001 to about 0.0003 mM, from about 0.0003 to about 0.001 mM, from about 0.001 to about 0.003 mM, from about 0.003 to about 0.01 mM, from about 0.01 to about 0.03 mM, from about 0.03 to about 0.1 mM, from about 0.1 to about 0.3 mM, from about 0.3 to about 1 mM, from about 1 to about 3 mM, from about 3 to about 10 mM, from about 10 to about 30 mM, or from about 30 to about 100 mM in water at 25° C. and atmospheric pressure. In one embodiment, a compound comprising Formula (I) may have a CMC of less than about 1 mM in water at 25° C. and atmospheric pressure. In another embodiment, a mixture of compounds having Formula may have a CMC of less than about 0.3 mM in water at 25° C. and atmospheric pressure.

The compounds comprising Formula (I) or mixtures of compounds comprising Formula (I) are substantially soluble in aqueous solutions. In general, the solubility of a compound comprising Formula (I) or a mixture of compounds comprising Formula (I) may range from about 10 mM to greater than about 2,000 mM in water at 25° C. and atmospheric pressure. In various embodiments, a compound comprising Formula (I) or a mixture of compounds comprising Formula (I) may have a solubility in water of at least about 20 mM, at least about 50 mM, at least about 100 mM, at least about 200 mM, at least about 500 mM, at least about 1,000 mM, at least about 2,000 mM, or greater than about 2,000 mM.

The compounds comprising Formula (I) or mixtures of compounds comprising Formula (I) have low surface tensions. In general, a compound comprising Formula (I) or a mixture of compounds comprising Formula (I) has a surface tension that ranges from about 15 mN/m to about 50 mN/m at CMC (and at 25° C. and atmospheric pressure). In certain embodiments, a compound comprising Formula (I) or a mixture of compounds comprising Formula (I) may have a surface tension of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mN/m at CMC (and at 25° C. and atmospheric pressure).

Additionally, the compounds comprising Formula (I) or mixtures of compounds comprising Formula (I) are substantially biodegradable. In general, 20-70% of a compound comprising Formula (I) or a mixture of compounds comprising Formula (I) will be degraded by microorganisms over a period of 28 days. In various embodiments, at least 20%, 25%, 30%, 35%, 40%, 45%, 50%, 55%, 60%, 65%, or 70% of a compound comprising Formula (I) or a mixture of compounds comprising Formula (I) may be biodegraded over a period of 28 days.

The compounds comprising Formula (I) or mixtures of compounds comprising Formula (I) are substantially non-toxic to marine organisms. In general, the EC50 or LD50 of a compound comprising Formula (I) or a mixture of compounds comprising Formula (I) to freshwater algae, invertebrates, or fish is about the same or less than those of alcohol ethoxylates (such as, polyoxyethylene (4) lauryl ether).

(d) Stereochemistry

The compounds disclosed herein generally have chiral centers. For example, possible chiral carbons in a compound comprising Formula (I) are denoted with asterisks in the schematic below. The compounds may comprise additional chiral centers (e.g., sulfur, nitrogen, etc.).

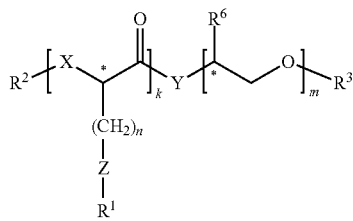

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, etc.

(e) Optional Additional Agents

In some embodiments, a compound comprising Formula (I) or a mixture of compounds comprising Formula (I) may be part of a composition. The composition may further comprise at least one agent chosen from pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, preservatives, coloring agents, fragrance agents, or combinations thereof.

In some embodiments, the composition may comprise at least one pH regulating agent. Non-limiting examples of suitable pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; organic bases (such as, for example, pyridine, triethylamine (i.e., monoethanol amine), diisopropylethylamine, N methylmorpholine, N,N dimethylaminopyridine); and combinations of any of the above.

In other embodiments, the composition may comprise at least one stain-removing enzyme. Suitable enzymes include but are not limited to proteases, peptidases, subtilisin, mannanases, amylases, carbohydrases, and lipases.

In still other embodiments, the composition may comprise at least one different type of surfactant. For example, the different surfactant may be another class of nonionic surfactant, an anionic surfactant, or a cationic surfactant. Non-limiting examples of suitable nonionic surfactants (including zwitterionic surfactants that have no net charge) include alcohol ethoxylates, alkyl phenol ethoxylates (e.g., nonylphenyl ethoxylate), thiol ethoxylates, fatty acid ethoxylates, glycerol esters, hexitol esters, amine ethoxylates, alkylamide ethoxylates, and imide ethoxylates. Suitable anionic surfactants include, but are not limited to, alkyl sulfates, alkyl ether sulfates, sulfated alkanolamides, glyceride sulfates, dodecyl benzene sulfonates, alkylbenzene sulfonates, alpha olefin sulfonates, and sulfocarboxylic compounds. Exemplary anionic surfactants include sodium dodecylbenzene sulfonate, and sodium methyl cocoyl taurate. Non-limiting examples of suitable cationic surfactants include alkyl amines, quaternary alkyl ammoniums, ester amines, and ether amines.

In further embodiments, the composition may comprise at least one optical brightener. Optical brighteners (also known as optical brightening agents, fluorescent brightening agents, or fluorescent whitening agents) are dyes that absorb light in the ultraviolet and violet region and reemit light in the blue regions. Non-limiting examples of suitable optical brightening agents include triazine-stilbenes, coumarins, imidazolines, diazoles, triazoles, benzoxazolines, and biphenyl-stilbenes. In one embodiment, the optical brightening agent may be a sulfonated tetrabenzotetraaza porphyrin derivative. In some embodiments, the optical brightening agent may be used in combination with a polyol, such as polyethylene glycol, polypropylene glycol, or polyvinyl alcohol.

In still other embodiments, the composition may comprise at least one bleaching agent. Suitable bleaching agents include without limit hydrogen peroxide, peroxy acid, sodium perborate, sodium percarbonate, sodium hypochlorite, and sodium dichloroisocyanurate.

In some embodiments, the composition may comprise at least one thickening agent (or theological additive). Suitable thickening agents include but are not limited to cellulosic ethers (such as hydroxycellulose, hydroxypropyl cellulose, hydroxymethylpropyl cellulose, hydroxyethyl cellulose, carboxymethyl cellulose, methylhydroxyethyl cellulose), polyvinylpyrrolidone, poly(vinylpyridine-N-oxide), bentonites, starches, gums, and combinations thereof.

In certain embodiments, the composition may comprise at least one scale inhibitor. Non-limiting examples of suitable scale inhibitors include phosphonates, sodium hexametaphosphate, sodium tripolyphosphate, oxalic acid, phosphoric acid, sulfamic acid, and carboxymethyl inulin.

In other embodiments, the composition may comprise at least one chelating agent. Suitable chelating agents include but are not limited to EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, DTPMP, and combinations thereof.

In further embodiments, the composition may comprise at least one water softening agent. Non-limiting examples of suitable water softening agents include sodium triphosphate, sodium tripolyphosphate, sodium carbonate, sodium silicate, zeolites, and citric acid.

In some embodiments, the composition may comprise at least one foam control agent, such as ethylene oxide/propylene oxide copolymers or silicone.

In still other embodiments, the composition may comprise at least one dispersant. Suitable dispersants include without limit phosphonates, carboxymethyl inulin, sodium hexametaphosphate, sodium tripolyphosphate, tetrasodium pyrophosphate, potassium tripolyphosphate, acrylic polymers, and combinations thereof.

In other embodiments, the composition may comprise at least one hydrotrope. Hydrotropes are compounds that improve the solubility of surfactants in aqueous solutions. Non-limiting examples of suitable hydrotropes include sodium toluenesulfonate, potassium toluene sulfonate, sodium xylene sulfonate, potassium xylene sulfonate, ammonium xylene sulfonate, sodium cumene sulfonate, ammonium cumene sulfonate, alkyl glucoside, complex coco imino glycinate, complex coco imino dipropionate, octyl imino dipropionate, phosphate ester potassium salt, and quaternary fatty methyl amine ethoxylate.

In yet alternate embodiments, the composition may comprise at least one linker. Linkers are amphiphiles that are used to increase surfactant-water interactions (i.e., hydrophilic linkers) or surfactant-oil interactions (i.e., lipophilic linkers). Suitable hydrophilic linkers include without limit alkyl naphthalene sulfonates such as mono- or di-methyl naphthalene sulfonate and diisopropyl naphthalene sulfonate. Non-limiting examples of suitable lipophilic linkers include hydrocarbyl alcohols having 8 or more carbon atoms in the principal chain or their low ethoxylated derivatives.

In other embodiments, the composition may comprise at least one filler. Non-limiting examples of suitable fillers include cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, talc, modified starches, lactose, sucrose, mannitol, sorbitol, and combinations thereof.

In still other embodiments, the composition may comprise at least one disintegrant. Suitable disintegrants include without limit starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth, and combinations thereof.

In other embodiments, the composition may comprise at least one a preservative. Non-limiting examples of suitable preservatives include antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, sodium hypochlorite, and combinations thereof.

In still other embodiments, the composition may comprise at least one coloring agent. Suitable coloring agents include, but are not limited to, food, drug and cosmetic colors (FD&C), drug and cosmetic colors (D&C), external drug and cosmetic colors (Ext. D&C), and other dyes known in the industry.

In further embodiments, the composition may comprise at least one fragrance (or perfume) agent. Suitable fragrance (or perfume) agents are well known in the art.

The weight fraction of the optional additional agents in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In various embodiments, the composition may be a liquid solution, an aqueous solution, an emulsion, a gel, a paste, a powder, a granular mixture, a pelleted mixture, or a solid.

(II) Polymers (a) Structure

Also provided herein are polymers comprising three different monomeric subunits. Thus, the polymers are terpolymers comprising:

a) at least one subunit A having the following structure:

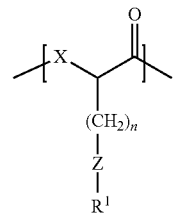

b) at least one subunit B having the following structure:

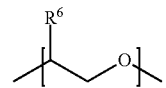

and c) at least one subunit C, optionally unsaturated, having the following structure:

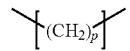

wherein:
$R^1$ is hydrocarbyl or substituted hydrocarbyl;
$R^6$ is hydrogen or alkyl;
X is O or NH; and
Z is sulfur, sulfoxide, sulfone, or selenium;
n is an integer of 1 or greater; and
p is an integer of 3 or greater.

In various embodiments, $R^1$ may be alkyl, alkenyl, alkynyl, aryl, substituted alkyl, substituted alkenyl, substituted alkynyl, or substituted aryl. In embodiments in which the terpolymer comprises more than one A subunit, $R^1$ in each subunit may differ. In exemplary embodiments, $R^1$ may be $C_1$ to $C_{10}$ alkyl, with the alkyl being linear, branched, or cyclic. In specific embodiments, $R^1$ may be methyl, ethyl, propyl, isopropyl, butyl, tert-butyl, hexyl, cyclohexyl, and the like. In specific embodiments, $R^1$ may be methyl.

In some embodiments, X may be O. In other embodiments, X may be NH. In certain embodiments, Z may be sulfur. In other embodiments, Z may be sulfoxide. In still other embodiments, Z may be sulfone. In yet other embodiments, Z may be selenium. In embodiments in which the terpolymer comprises more than one A subunit, X and Z in each subunit may differ.

In certain embodiments, $R^6$ may be hydrogen, $C_1$ to $C_{10}$ alkyl, or $C_1$ to $C_6$ alkyl, with the alkyl being linear or branched. In embodiments in which the terpolymer comprises more than one B subunit, $R^6$ in each subunit may differ. In some embodiments, $R^6$ may be hydrogen, methyl, or ethyl. In exemplary embodiments, $R^6$ may be hydrogen.

In certain embodiments, n may range from 1 to about 20, or from 1 to about 10. In some embodiments, n may range from about 1 to about 6. In specific embodiments, n may be 1, 2, 3, or 4. In embodiments in which the terpolymer comprises more than one A subunit, n in each subunit may differ.

In various embodiments, p may range from 3 to about 500 in each subunit. In certain embodiments, p may range from about 3 to about 36 in each subunit. In some embodiments, p may range from 6 to 30 or from 8 to 22 in each subunit C. In embodiments in which the terpolymer comprises more than one C subunit, p in each subunit may differ. Thus, the total number of p in a terpolymer may be more than 500.

In certain embodiments, $R^1$ may be $C_1$ to $C_{10}$ alkyl, $R^6$ may be hydrogen or $C_1$ to $C_{10}$ alkyl, n may range from 1 to 10, and p may range from 3 to 200. In specific embodiments, $R^1$ may be methyl; $R^6$ may be hydrogen or methyl, X may be oxygen, Z may be sulfur or sulfoxide, n may be 2, and p may range from 6 to 30.

In general, the terpolymers may contain any number of repeats of each subunit, and the subunits may be arranged in any order. In general, the number of repeats of a subunit is presented as an average number (meaning that the number of repeats of a subunit can vary in a population of terpolymers). In some embodiments, each subunit may be repeated up to several thousand times. In various embodiments, each subunit independently may be repeated at least 1, 2, 3, 4, 5, 6, 7, 8, 9, 10, 12, 14, 16, 18, 20, 25, 30, 35, 40, 50, 60, 70, 80, 90, 100, 120, 140, 160, 180, 200, 250, 300, 350, 400, 450, 500, 1000, 2000, 3000, 4000, 6000, 8000, 10,000, or more times. In specific embodiments, each subunit independently may be repeated up to about 500 times. The repeats of a subunit may be contiguous (i.e., tandemly repeated). For example, the terpolymer may be $A_{20}B_{100}C_{p=36}$, $C_{p=20}A_{30}B_{200}$, and the like. Alternatively, the repeats of a subunit may be interspersed among the other subunits (i.e., randomly repeated). For example, the terpolymer may be $C_{p=20}A_{10}B_{50}C_{p=20}$, $A_5B_{50}C_{p=30}B_{50}A_5$, and so forth.

The number average molecular weight ($M_n$) of the terpolymers disclosed herein can and will vary. In general, the $M_n$ of a polymer is greater than about 300. In various embodiments, the $M_n$ of the polymer may range from about 300 to about 600, from about 600 to about 1200, from about 1200 to about 2400, from about 2400 to about 4800, from about 4800 to about 10,000, from about 10,000 to about 30,000, from about 30,000 to about 100,000, from about 100,000 to 300,000, from about 300,000 to about 1,000,000, or larger than about 1,000,000.

The terpolymers disclosed herein generally have a narrow molecular mass distribution. The polydispersity index ($PDI=M_w/M_n$) is generally less than about 1.8. In some embodiments, the PDI is less than about 1.7, less than about 1.6, less than about 1.5, less than about 1.4, less than about 1.3, less than about 1.2, or less than about 1.1.

In some embodiments, the terpolymer may further comprise at least one linker. In general, the linker comprises at least one atom, and serves to join or link two of the different subunits. In some embodiments, the linker may be a heteroatom, such as oxygen, nitrogen, sulfur, phosphorous, and the like. In other embodiments, the linker may be hydrocarbyl or substituted hydrocarbyl. For example, the linker may be alkyl, substituted alkyl, carbonyl, ester, amide, and so forth.

(b) Properties of the Terpolymers

The terpolymers disclosed herein generally have a critical micelle concentration (CMC) in water at 25° C. and atmospheric pressure. For example, the CMC of a disclosed terpolymer may range from about 0.0001 to about 100 mM in water at 25° C. and atmospheric pressure. In various embodiments, a terpolymer may have a CMC that ranges from about 0.0001 to about 0.0003 mM, from about 0.0003 to about 0.001 mM, from about 0.001 to about 0.003 mM, from about 0.003 to about 0.01 mM, from about 0.01 to about 0.03 mM, from about 0.03 to about 0.1 mM, from about 0.1 to about 0.3 mM, from about 0.3 to about 1 mM, from about 1 to about 3 mM, from about 3 to about 10 mM, from about 10 to about 30 mM, or from about 30 to about 100 mM in water at 25° C. and atmospheric pressure. In specific embodiments, a terpolymer disclosed herein may have a CMC of less than about 1 mM in water at 25° C. and atmospheric pressure.

The terpolymers disclosed herein are highly soluble in aqueous solutions. In general, the solubility of a terpolymer may range from about 10 mM to greater than about 2,000 mM in water at 25° C. and atmospheric pressure. In various embodiments, a terpolymer may have a solubility in water of at least about 20 mM, at least about 50 mM, at least about 100 mM, at least about 200 mM, at least about 500 mM, at least about 1,000 mM, at least about 2,000 mM, or greater than about 2,000 mM.

In general, the terpolymers have low surface tensions. Typically, a terpolymer has a surface tension that ranges from about 15 mN/m to about 50 mN/m at CMC (and at 25° C. and atmospheric pressure). In certain embodiments, a terpolymer may have a surface tension of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mN/m at CMC (and at 25° C. and atmospheric pressure).

Additionally, the terpolymers are substantially biodegradable. In general, 20-70% of a terpolymer will be degraded by microorganisms over a period of 28 days. In various embodiments, at least 20%, 25%, 30%, 35%, 40%, 45%, 50%, 55%, 60%, 65%, or 70% of a terpolymer may be biodegraded over a period of 28 days.

The terpolymers disclosed are substantially nontoxic to marine organisms. In general, the EC50 or LD50 of a terpolymer to freshwater algae, invertebrates, or fish is about the same or less than those of alcohol ethoxylates (such as, e.g., polyoxyethylene (4) lauryl ether).

(c) Optional Additional Agents

In some embodiments, a terpolymer disclosed herein may be part of a composition. The composition may further comprise at least one agent chosen from pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, preservatives, coloring agents, fragrance agents, or combinations thereof. Examples of each of the agents are presented above in section (I)(e).

(III) Processes for Preparing Compounds Comprising Formula (I)

Another aspect of the disclosure provides processes for preparing compounds comprising Formula (I):

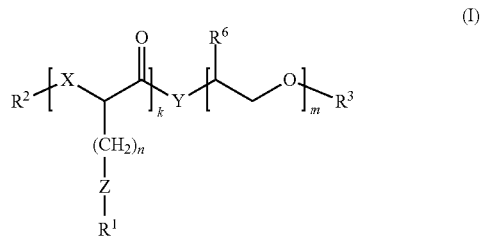

(I)

wherein $R^1$, $R^2$, $R^3$, $R^6$, X, Y, Z, m, n, and k are as defined above. Those of skill in the art will appreciate that the compounds comprising Formula (I) may be prepared by a variety of processes.

(a) Preparation of Ester Compounds

In embodiments in which Y in Formula (I) is O, such ester compounds may be prepared by contacting a compound comprising Formula (III) with a hydrophobic alcohol ethoxylate to form a compound comprising Formula (Ia) according to the reaction scheme shown below:

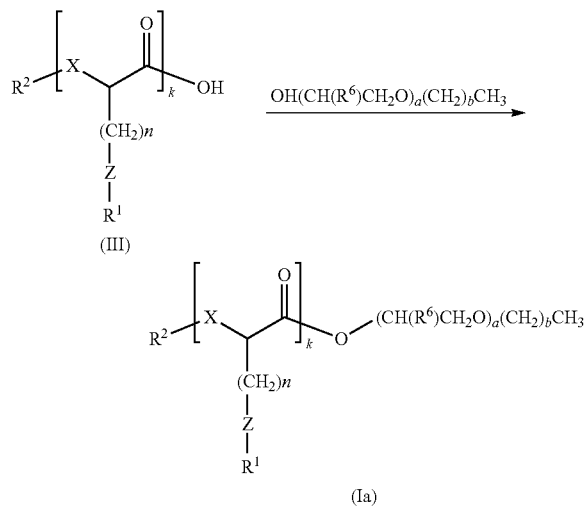

wherein $R^1$, $R^2$, $R^6$, X, Z, n, and k are as defined above, a is an integer of 1 or greater, and b is an integer of 2 or greater.

(i) Esterification Reaction

The amount of hydrophobic alcohol ethoxylate contacted with the compound comprising Formula (III) can and will vary. In general, the mole-to-mole ratio of the compound comprising Formula (III) to the hydrophobic alcohol ethoxylate may range from about 1:0.01 to about 1:2. In various embodiments, the mole-to-mole ratio of the compound comprising Formula (III) to the hydrophobic alcohol ethoxylate may be about 1:0.01, about 1:0.02, about 1:0.04, about 1:0.06, about 1:0.08, about 1:0.1, about 1:0.2, about 1:0.3, about 1:0.4, about 1:0.5, about 1:0.6, about 1:0.7, about 1:0.8, about 1:0.9, about 1:1.0, about 1:1.1, about 1:1.2, about 1:1.3, about 1:1.4, about 1:1.5, about 1:1.6, about 1:1.7, about 1:1.8, or about 1:2.0.

In general, contact between the compound comprising Formula (III) and the hydrophobic alcohol ethoxylate is conducted in the presence of a catalyst. The catalyst may be a chemical catalyst, such as a proton donor. Alternatively, the catalyst may be an enzyme catalyst, such as a lipase enzyme. Lipase enzymes can catalyze the formation (as well as hydrolysis) of ester linkages.

In embodiments in which the catalyst is a proton donor, a variety of proton donors may be used in the process. Non-limiting examples of suitable proton donor include acid salts (e.g., sodium or potassium bicarbonates, bisulfates, hydrosulfates, or phosphates), mineral acids (e.g., hydrogen halides such as hydrochloric acid, hydrobromic acid; halogen oxoacids such as hypochloric acid, chloric acid, perchloric acid, periodic acid; sulfuric acid; boric acid; nitric acid, phosphoric acid, etc.); sulfonic acids (e.g., methanesulfonic acid, p-toluenesulfonic acid); solid bound proton donors (e.g., Amberlyst 15, Amberlyst 35, and the like); ion exchange resins (e.g., Amberlite, Amberjet, Dowex, etc.); ionomers (e.g., polystyrene sulfonate, Nafion, Hycar and so forth); and ionic liquids having acidic characteristics. In exemplary embodiments, the proton donor is p-toluenesulfonic acid.

The mole-to-mole ratio of the compound comprising Formula (III) to the proton donor can and will vary depending upon the identity of the proton donor. In general, the mole-to-mole ratio of the compound comprising Formula (III) to the proton donor may range from about 1:0.005 to about 1:0.25. In some embodiments, the mole-to-mole ratio of the compound comprising Formula (III) to the proton donor may be about 1:0.01, about 1:0.02, about 1:0.04, about 1:0.05, about 1:0.06, about 1:0.08, about 1:0.10, about 1:0.12, about 1:0.14, about 1:0.16, about 1:0.18, or about 1:0.20.

The reaction may be conducted in the absence of a solvent or in the presence of a solvent. In embodiments in which a solvent is present, the type of solvent may vary depending upon the reactants. Thus, the solvent may be a nonpolar solvent, a protic polar solvent, an aprotic polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Suitable protic polar solvents include without limit amides such as formamide, acetamide, and the like. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be toluene.

The volume-to-mass ratio of the solvent to the compound comprising Formula (III) can and will vary. Typically, the volume-to-mass ratio of the solvent to the compound comprising Formula (III) may range from about 1:1 to about 100:1. In various embodiments, the volume-to-mass ratio of the solvent to the compound comprising Formula (III) may range from about 1:1 to about 3:1, from about 3:1 to about 10:1, from about 10:1 to about 30:1, or from about 30:1 to about 100:1. In preferred embodiments, the volume-to-mass ratio of the solvent to the compound comprising Formula (III) may range from about 4:1 to about 10:1.

The reaction may be conducted at a temperature that ranges from about 30° C. to about 200° C. In certain embodiments, the temperature of the reaction may be about 40° C., 50° C., 60° C., 70° C., 80° C., 90° C., 100° C., 110° C., 120° C., 130° C., 140° C., or 150° C. In preferred embodiments, the reaction may be conducted at a temperature from about 100-115° C. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compound comprising Formula (III) and a significantly increased amount of the ester compound comprising Formula (Ia) compared to the amounts of each present at the beginning of the reaction.

The compound comprising Formula (Ia) may be isolated from the reactants in the reaction mixture by means known in the art. Suitable means include extracting, washing, precipitating, filtering, distilling, evaporating, drying, chromatography, and combinations thereof.

The yield of the compound comprising Formula (Ia) can and will vary. In general, yield of the compound will be at least about 20%, at least about 30%, at least about 40%, at least about 50%, at least about 60%, at least about 70%, at least about 80%, or at least about 90%.

(ii) Optional Oxidation Reaction

In embodiments in which Z is sulfur, a compound comprising either Formula (III) or Formula (Ia) may be contacted with an oxidizing agent to convert the sulfur to a sulfoxide (or a sulfone). A variety of oxidizing agents may be used for this reaction. Non-limiting examples of suitable oxidizing agents include peroxy acids (e.g., chloroperoxybenzoic acid, peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benezeneselenic acid, lead tetraacetate, osmium tetroxide, phosphomolybdic acid hydrate, pyridinium chlorochromate, pyridinium dichromate, quinolinium dichromate, and the like). and combinations thereof. In specific embodiments, the oxidizing agent may be hydrogen peroxide.

The mole-to-mole ratio of the sulfur-containing compound to the oxidizing agent can and will vary. In general, the mole-to-mole ratio of the sulfur-containing compound to the oxidizing agent may range from about 1:0.1 to about 1:20. In various embodiments, the mole-to-mole ratio of the sulfur-containing compound to the oxidizing agent may be about 1:1.0, 1:1.5, 1:2.0, 1:2.4, 1:2.6, 1:2.8, 1:3.0, 1:3.2, 1:3.6, or 1:4.0. In exemplary embodiments, the mole-to-mole ratio of the sulfur-containing compound to the oxidizing agent may be about 1:3.

The oxidation reaction may be performed in the presence of a solvent. The solvent may be a nonpolar solvent, a protic solvent, an aprotic solvent, or a combination thereof, depending upon the reactants. Suitable solvents are listed above in section III(a)(i). In preferred embodiments, the solvent may be methanol.

The volume-to-mass ratio of the solvent to the sulfur-containing compound can and will vary. Typically, the volume-to-mass ratio of the solvent to the sulfur-containing compound may range from about 1:1 to about 40:1. In various embodiments, the volume-to-mass ratio of the solvent to the sulfur-containing compound may be about 1:1, about 2:1, about 3:1, about 4:1, about 5:1, about 6:1, about 8:1, about 10:1, about 20:1, or about 30:1. In specific embodiments, the volume-to-mass ratio of the solvent to the sulfur-containing compound may range from about 2.5:1 to about 5:1.

The oxidation reaction may be conducted at a temperature that ranges from about −10° C. to about 50° C. In certain embodiments, the temperature of the reaction maybe about 0° C., 10° C., 20° C., 25° C., or 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art. In this context, the final reaction mixture contains a significantly diminished amount of the sulfur-containing compound and a significantly increased amount of the sulfoxide compound compared to the amounts of each present at the beginning of the reaction.

The sulfoxide (or sulfone) compound may be isolated from the reactants in the reaction mixture by means well known in the art. Suitable means include extracting, washing, precipitating, filtering, distilling, evaporating, drying, chromatography, chiral chromatography, and combinations thereof.

The yield of the sulfoxide (or sulfone) compound of either Formula (III) or Formula (Ia) can and will vary. In general, the yield of the sulfoxide (or sulfone) compound will be at least about 20%, at least about 30%, at least about 40%, at least about 50%, at least about 60%, at least about 70%, at least about 80%, or at least about 90%.

(b) Preparation of Amide Compounds

In embodiments in which Y in Formula (I) is NH, such amide compounds may be prepared by a variety of different processes. For example, amide compounds of Formula (I) can be prepared by a process comprising an activation step and an amide bond formation step (See, e.g., Montalbetti et al., 2005, Tetrahedron 61:10827-52; Valeur et al., 2009, Chem. Soc. Rev. 38:606-31; Joullie et al., ARKIVOC 2010 (viii)189-250). Those skilled in the art understand that a variety of activating agents (e.g., acyl halides, acyl azides, anhydrides, etc.) may be used in the activation step. Similarly, a variety of amines (e.g., primary or secondary amines, mono-, di-, or triamine ethoxylates, etc.) are suitable for use in the amide bond formation step. Alternatively, amide compounds of Formula (I) can be prepared by direct amidation (see Example 19).

In some embodiments, an amide of Formula (I) may be prepared by contacting a compound comprising Formula (III) with an activating agent to form a compound comprising Formula (II), which is then contacted with a hydrophobic amine ethoxylate to form the amide compound of Formula (Ib) according to the reaction scheme shown below:

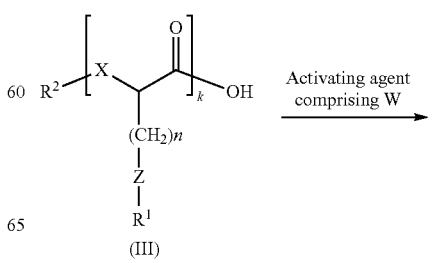

-continued

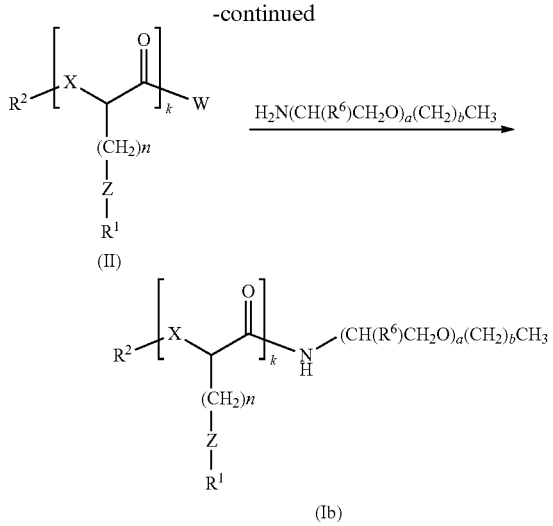

wherein $R^1$, $R^2$, $R^6$, X, Z, n, and k are as defined above, a is an integer of 1 or greater, b is an integer of 2 or greater, and W is a leaving group.

(i) Activation Reaction

The first step of the process comprises contacting a compound of Formula (III) with an activating agent comprising a leaving group, W, to form a compound comprising Formula (II). A variety of activating agents may be used in this step of the process. Non-limiting examples of suitable activating agents include thionyl halides (e.g., thionyl chloride, thionyl bromide, thionyl fluoride), acyl halides, acyl azides, anhydrides (e.g., carboxylic anhydrides, carbonic anhydrides, N-carboxy anhydrides), ester (e.g., alkyl esters, succinimidyl esters), and combinations thereof. In exemplary embodiments, the activating agent may be thionyl chloride.

The mole-to-mole ratio of the compound comprising Formula (III) to the activating agent can and will vary. In general, the mole-to-mole ratio of the compound comprising Formula (III) to the activating agent may range from about 1:1 to about 1:20. In various embodiments, the mole-to-mole ratio of the compound comprising Formula (III) to the activating agent may be about 1:2, 1:3, 1:4, 1:5, 1:6, 1:7, 1:8, 1:9, or 1:10. In a preferred embodiment, the mole-to-mole ratio of the compound comprising Formula (III) to the activating agent may be about 1:5.

Contact with the activating agent may occur in the presence of a solvent. In general, the type of solvent used will depend upon the identity of the compound comprising Formula (III). Suitable nonpolar, aprotic, and protic solvents are detailed above in section (III)(a)(i). In exemplary embodiments, the solvent may be dichloromethane. Typically, the weight-to-weight ratio of the solvent to the compound comprising Formula (III) may range from about 1:1 to about 100:1. In preferred embodiments, the weight-to-weight ratio of the solvent to the compound comprising Formula (III) may range from about 4:1 to about 30:1.

Contact with the activating agent may occur at a temperature that ranges from about −10° C. to about 50° C. In certain embodiments, the temperature of the reaction may be about 0° C., 10° C., 20° C., 25° C., or 30° C. In one preferred embodiment, the reaction may be allowed to proceed at about 0° C. In another preferred embodiment, the temperature of the reaction may be room temperature. In another preferred embodiment, the reaction may be allowed to proceed for a first period of time at 0° C. and a second period of time at room temperature. Typically, the reaction will be conducted at atmospheric pressure.

The period of time of contact with the activating agent can and will vary. In general, the duration of time may range from about 0.5 hour to about 10 hours. In various embodiments, duration of the reaction may be about 1, 1.5, 3, 2.5, 3, 3.5, 4, 4.5 or 5 hours.

Upon completion of the reaction, a portion of the solvent may be removed from the reaction mixture using methods known to those skilled in the art. Alternatively, the compound comprising Formula (II) may be isolated from the reaction mixture using well known techniques.

(ii) Amidation Reaction

The second step of the process comprises contacting the compound comprising Formula (II) with a hydrophobic amine ethoxylate to form the amide compound comprising Formula (Ib). Hydrophobic amine ethoxylates may be obtained commercially, or hydrophobic amine ethoxylates may be prepared, for example, as described in International Patent Application WO 2013059107, the disclosure of which is incorporated herein in its entirety.

The amount of hydrophobic amine ethoxylate contacted with the compound comprising Formula (II) can and will vary. In general, the mole-to-mole ratio of the compound comprising Formula (II) to the hydrophobic amine ethoxylate may range from about 1:0.5 to about 1:3. In various embodiments, the mole-to-mole ratio of the compound comprising Formula (II) to the hydrophobic amine ethoxylate may be about 1:0.6, about 1:0.7, about 1:0.8, about 1:0.9, about 1:1.0, about 1:1.1, about 1:1.2, about 1:1.3, about 1:1.4, about 1:1.5, about 1:1.6, about 1:1.7, about 1:1.8, or about 1:2.0.

In some embodiments, the amidation reaction may be conducted in the presence of a proton acceptor. A variety of proton acceptors are suitable for use in this reaction. Non-limiting examples of suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), amines (such as, for example methylamine, dimethylamine, trimethylamine, ethylamine, diethylamine, triethylamine, propylamine, isopropylamine, diisopropylethylamine, and the like), organic bases (such as, for example, pyridine, N methylmorpholine, N,N dimethylaminopyridine), and mixtures of any of the above.

The mole-to-mole ratio of the compound comprising Formula (II) to the proton acceptor can and will vary depending upon the identity of the proton acceptor. In general, the mole-to-mole ratio of the compound comprising Formula (II) to the proton acceptor may range from about 1:0.01 to about 1:10. In various embodiments, the mole-to-mole ratio of the compound comprising Formula (II) to the proton acceptor may be about 1:0.5, 1:0.1, 1:0.5, 1:1, 1:1.5, 1:2, 1:3, 1:4, or 1:5. In exemplary embodiments, the mole-to-mole ratio of the compound comprising Formula (II) to the proton acceptor may be about 1:2.

The amidation reaction may be conducted at a temperature that ranges from about −10° C. to about 50° C. In certain embodiments, the reaction may be allowed to proceed at about 0° C., 10° C., 20° C., 25° C., or 30° C. In a preferred embodiment, the reaction may commence at about 0° C. and slowly warm to room temperature over a period of time. In general, the reaction will be conducted at atmospheric pressure.

The duration of the reaction can and will vary. In general, the reaction may be allowed to proceed overnight (i.e., about 15-18 hours). Typically, however, the reaction may be allowed to proceed for a sufficient period of time until the reaction is complete, as determined by means well known to those of skill in the art.

The compound comprising Formula (Ib) may be isolated from the reaction mixture by means well known in the art. Suitable means include extracting, washing, precipitating, filtering, distilling, evaporating, drying, chromatography, and combinations thereof. In specific embodiments, the compound comprising Formula (Ib) may be isolated using chromatography.

The yield of the compound comprising Formula (Ib) can and will vary. In general, yield of the compound comprising Formula (Ib) will be at least about 20%, at least about 30%, at least about 40%, at least about 50%, at least about 60%, at least about 70%, at least about 80%, or at least about 90%.

(iii) Optional Oxidation Reaction

In embodiments in which Z in any of the compounds comprising Formulas (III), (II), or (Ib) is sulfur, the sulfur-containing compound may be contacted with an oxidizing agent essentially as described above in section III(a)(ii) to convert the sulfur to a sulfoxide (or sulfone).

(iv) Optional Protecting and Unprotecting Reactions

In embodiments in which $R^2$ in the compound comprising Formula (III) is hydrogen, the alcohol or amine group of the compound comprising Formula (III) may be protected with a protecting group prior to the activation reaction. Suitable protecting groups and means for attaching the protecting group are well known in the art. A variety of protecting groups and the synthesis thereof may be found in "Protective Groups in Organic Synthesis" by T. W. Greene and P. G. M. Wuts, John Wiley & Sons, 2006. Upon completion of the amidation reaction (and prior to or following the optional oxidation reaction), the protecting group may be removed from the compound comprising Formula (Ib) using techniques well known in the art.

(IV) Processes for Preparing Terpolymers

Also provided herein are processes for preparing the terpolymers disclosed herein. In particular, the terpolymers may be prepared using any of the processes or combinations of the processes detailed above in section (III). For example, the processes may be performed in any order, may be performed repeatedly, and/or may be performed in conjunction with polymerization, alkylation, esterification, amidation, or other reactions well known in the art.

(V) Applications and Uses Thereof

The compounds, mixtures of compounds, or terpolymers disclosed herein may be used in a variety of applications. In general, the usefulness of the compounds, mixtures of compounds, or terpolymers relates to their surfactant qualities.

In general, the compounds, mixtures of compounds, or terpolymers of the invention may be used as detergents, wetting agents, emulsifiers, foaming agents, or dispersants. Suitable uses of detergents, wetting agents, emulsifiers, foaming agents, and dispersants are well known in the art. Non-limiting examples of suitable uses include laundry detergents, laundry pre-wash products, fabric softeners, automatic dishwasher detergents, hand dishwashing liquids, household detergents, household cleaners, solid surface cleaners, floor cleaners, floor polishes, upholstery cleaners, auto cleaners, institutional cleaners, laboratory cleaners, detergents for biochemistry/biotechnology applications, personal care products, hand cleaners, shampoos, hair conditioners, hair styling products, hair coloring products, facial cleaners, toothpaste, cosmetics, laxatives, industrial cleaners, industrial surfactants, industrial emulsifiers, paints, adhesives, inks, quantum dot coatings, anti-fogs, ski or snowboard waxes, oil additives, textile processing (e.g., pre-scouring, desizing, and/or finishing applications), wool processing, metal processing (e.g., cutting oils and water-based hydraulic fluids), agricultural applications (e.g., emulsifiable concentrates; soil wetting agents; agrochemical formulations), latex production (e.g., emulsion polymerization), paper processing, paper de-inking, oil harvesting, refining, or processing (e.g., crude oil drilling fluids and demulsifiers, mobilization of oil in oil wells, liquid drag reducing agent in pipelines), oil reclamation processes, and so forth.

The amount of the compound, mixture of compounds, or terpolymer used in the various applications can and will vary. In general, the amount of the compound, mixture of compounds, or terpolymer used in a specific application will depend upon a variety of factors, including the type of application.

An exemplary use of the compounds, mixtures of compounds, and terpolymers disclosed herein is in detergents, for example laundry detergents.

(VI) Processes for Cleaning an Article

Another aspect of the disclosure provides processes for cleaning an article, wherein a process comprises contacting an article with a composition comprising at least one compound or at least one polymer of the invention. In some embodiments, the process may further comprise contacting the article with a solvent to remove the at least one compound or polymer of the invention. Typically, the solvent may be an aqueous solvent such as water.

In certain embodiments, the article may be an inanimate object. Non-limiting examples of suitable inanimate objects include as laundry items, dishes, flatware, cookware items, counters, floors, or other surfaces. As an example, the surface may be an oil contaminated surface, wherein the process entails removing the oil from the contaminated surface. In other embodiments, the article may be an animate object or a part of an animate object. Examples of suitable animate objects include but are not limited to hair, hands, face, and other body parts.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "amide" as used herein describes a compound comprising a carbonyl-nitrogen linkage.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The term "hydrophobic" refers to the physical property of a molecule (which is known as a hydrophobe) that is antagonistic to water (i.e., incapable of dissolving in water).

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

A "sulfoxide" refers to a compound containing a "sulfinyl" functional group that is attached to two carbon atoms. The sulfinyl group, as depicted as:

represents:

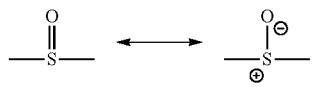

Having described the invention in detail, it will be apparent that modifications and variations are possible without departing from the scope of the invention defined in the appended claims.

EXAMPLES

The following examples illustrate various embodiments of the invention.

Example 1: Preparation of Oligomeric Terpolymer Obtained from Condensation of HMTBa and Polyoxyethylene (4) Lauryl Ether To 2-hydroxy-4-(methylthio)butanoic acid (88%, 5.00 g, 29.3 mmol) was added polyoxyethylene (4) lauryl ether (8.48 g, 23.4 mmol), p-toluenesulfonic acid (0.28 g, 1.47 mmol) and toluene (25 mL) in a round bottom flask that was fitted with a Dean-Stark trap and reflux condenser. The resulting mixture was heated to reflux with removal of water for approximately 16 hrs. The reaction was cooled to room temperature and then diluted with ethyl acetate (50 mL) and washed with sat. NaHCO$_3$ (3×50 ml), water (1×50 mL), brine (1×50 mL), dried over magnesium sulfate, filtered and evaporated on a rotavap to give a dark oil (11.6 g, 93%).

Example 2: Preparation of Oligomeric Terpolymer Obtained from Oxidation of the Condensation Products of HMTBa and Polyoxyethylene (4) Lauryl Ether To a solution of the material from Example 1 (11.5 g, 23.3 mmol) in methanol (60 mL) at 0° C. was added hydrogen peroxide (30%, 7.1 mL, 69.5 mmol). The reaction was allowed to warm to room temperature with stirring overnight. The reaction was diluted with DCM (500 mL) and washed with water (100 mL) and separated in a separatory funnel overnight. The organic layer was then washed with 10% sodium bisulfite (1×100 mL), dried over magnesium sulfate, filtered and evaporated to give a light yellow oil (10.2 g, 86%).

Example 3: Preparation of Oligomeric Terpolymer Obtained from Condensation of HMTBa and Polyoxyethylene (10) Cetyl Ether 2-hydroxy-4-(methylthio)butanoic acid (88%, 5.05 g, 29.6 mmol), polyoxyethylene (10) cetyl ether (16.1 g, 23.6 mmol), and p-toluenesulfonic acid (0.1 g, 0.53 mmol) were dissolved in toluene (25 mL) in a round-bottom flask. A Dean-Stark trap, reflux condenser, and nitrogen line were fitted to the flask. The solution was heated at reflux overnight. The reaction was cooled to room temperature and diluted with ethyl acetate (65 mL). The solution was washed with sat. sodium bicarbonate (3×25 mL) and a 50/50 by volume water/brine mixture (50 mL). The organic layer was dried with magnesium sulfate, filtered, evaporated on a rotavap, and dried on the high vacuum overnight to give a beige waxy solid (16.2 g, 81%).

Example 4: Preparation of Oligomeric Terpolymer Obtained from Oxidation of the Condensation Products of HMTBa and Polyoxyethylene (10) Cetyl Ether To a solution of the material from Example 3 (11.5 g, 14.2 mmol) in methanol (30 mL) cooled on an ice bath was slowly added 30% hydrogen peroxide (4.4 mL, 43.1 mmol). The ice bath was removed and the solution stirred overnight. The reaction was diluted with ethyl acetate (450 mL) and washed with water (100 mL) and 10% sodium bisulfite (100 mL). The organic layer was dried over magnesium sulfate, filtered, evaporated on a rotavap, and then dried under vacuum overnight to give a white waxy solid (7.18 g, 61%).

Example 5: Preparation of Oligomeric Terpolymer Obtained from Condensation of HMTBa and Polyoxyethylene (10) Stearyl Ether To 2-hydroxy-4-(methylthio)butanoic acid (88%, 5.25 g, 30.8 mmol), polyoxyethylene (10) stearyl ether (16.9 g, 23.8 mmol), and p-toluenesulfonic acid (0.33 g, 1.73 mmol) in a round bottom flask was added toluene (25 mL) to give a solution. A Dean-Stark trap, reflux condenser, and nitrogen line were fitted to the flask. The solution was heated at reflux overnight. The reaction was cooled to room temperature and diluted with ethyl acetate (25 mL). The solution was washed with sat. sodium bicarbonate (3×25 mL) and water (1×25 mL) and brine (25 mL). The organic layer was dried over magnesium sulfate, filtered, evaporated on a rotavap, and dried on the high vacuum overnight to give a beige waxy solid (19.4 g, 93%).

Example 6: Preparation of Oligomeric Terpolymer Obtained from Oxidation of the Condensation Products of HMTBa and Polyoxyethylene (10) Stearyl Ether To a solution of the material from Example 5 (11.02 g, 13.1 mmol) in methanol (30 mL) cooled on an ice bath was slowly added 30% hydrogen peroxide (4.0 mL, 39.2 mmol). The ice bath was removed and the solution stirred overnight. The reaction was diluted with ethyl acetate (350 mL) and washed with water (100 mL) and 10% sodium bisulfite (100 mL). The organic layer was dried over magnesium sulfate, filtered, evaporated on a rotavap, and dried on the high vacuum overnight to give a pale yellow waxy solid (6.93 g, 62%).

Example 7: Preparation of Oligomeric Terpolymer Obtained from Condensation of HMTBa and Polyoxyethylene (20) Cetyl Ether To 2-hydroxy-4-(methylthio)butanoic acid (88%, 4.13 g, 24.2 mmol), polyoxyethylene (20) cetyl ether (22.4 g, 19.9 mmol), and p-toluenesulfonic acid (0.8 g, 4.2 mmol) in a round bottom flask was added toluene (35 mL) to give a solution. A Dean-Stark trap, reflux condenser, and nitrogen line were fitted to the flask. The solution was heated at reflux overnight. The reaction was cooled to room temperature and diluted with ethyl acetate (65 mL). The solution was washed with sat. sodium bicarbonate (3×25 mL) and a 50/50 by volume water/brine mixture (50 mL). The organic layer was dried over magnesium sulfate, filtered, evaporated on a rotavap, and dried on the high vacuum overnight to give a brown waxy solid (19.7 g, 77%).

Example 8: Preparation of Oligomeric Terpolymer Obtained from Oxidation of the Condensation Products of HMTBa and Polyoxyethylene (20) Cetyl Ether To a solution of the material from Example 7 (15.0 g, 11.9 mmol) in methanol (40 mL) cooled on an ice bath was slowly added 30% hydrogen peroxide (3.7 mL, 36.2 mmol). The ice bath was removed and the solution stirred overnight. The reaction was diluted with ethyl acetate (350 mL) and washed with water (100 mL) and 10% sodium bisulfite (100 mL). The organic layer was dried with magnesium sulfate, filtered, evaporated on a rotavap, and dried on the high vacuum overnight to give a yellow waxy solid (3.72 g, 25%).

Example 9: Preparation of Oligomeric Terpolymer Obtained from Condensation of HMTBa and Polyoxyethylene (20) Stearyl Ether To 2-hydroxy-4-(methylthio)butanoic acid (88%, 4.01 g, 23.5 mmol), polyoxyethylene (20) stearyl ether (21.6 g, 18.8 mmol), and p-toluenesulfonic acid (0.35 g, 1.84 mmol) in a round-bottom flask was added toluene (35 mL). A Dean- Stark trap, reflux condenser, and nitrogen line were fitted to the flask. The solution was heated at reflux overnight. The reaction was cooled to room temperature and diluted with ethyl acetate (65 mL). The solution was washed with sat. sodium bicarbonate (3×25 mL) and a 50/50 by volume water/brine mixture (50 mL). The organic layer was dried over magnesium sulfate, filtered, evaporated on as rotavap and dried on the high vacuum overnight to give a beige waxy solid (21.2 g, 86%).

Example 10: Preparation of Oligomeric Terpolymer Obtained from Oxidation of the Condensation Products of HMTBa and Polyoxyethylene (20) Stearyl Ether To a solution of the material from Example 9 (14.9 g, 11.6 mmol) in methanol (40 mL) cooled on an ice bath was slowly added 30% hydrogen peroxide (3.9 mL, 38.2 mmol). The ice bath was removed and the solution stirred overnight. The reaction was diluted with ethyl acetate (350 mL) and washed with water (100 mL) and 10% sodium bisulfite (100 mL). The organic layer was dried over magnesium sulfate, filtered, evaporated on a rotavap, and dried on the high vacuum overnight to give a white waxy solid (5.76, 38%).

Example 11: Preparation of Oligomeric Terpolymer Obtained from Condensation of HMTBa and Polyoxyethylene (10) Oleyl Ether To 2-hydroxy-4-(methylthio)butanoic acid (88%, 6.12 g, 35.9 mmol), polyoxyethylene (10) oleyl ether (20.0 g, 28.2 mmol), and p-toluenesulfonic acid (0.38 g, 2.00 mmol) in a round-bottom flask was added toluene (35 mL). A Dean-Stark trap, reflux condenser, and nitrogen line were fitted to the flask. The solution was heated at reflux overnight. The reaction was cooled to room temperature and diluted with ethyl acetate (65 mL). The solution was washed with sat. sodium bicarbonate (3×25 mL) and a 50/50 by volume water/brine mixture (50 mL). The organic layer was dried over magnesium sulfate, filtered, evaporated on a rotavap and dried on the high vacuum overnight to give a dark brown oil (23.7 g, 96%).

Example 12: Preparation of Oligomeric Terpolymer Obtained from Oxidation of the Condensation Products of HMTBa and Polyoxyethylene (10) Oleyl Ether To a solution of the material from Example 11 (16.7 g, 19.8 mmol) in methanol (50 mL) cooled on an ice bath was slowly added 30% hydrogen peroxide (6.1 mL, 59.7 mmol). The ice bath was removed and the solution stirred overnight. The reaction was diluted with ethyl acetate (350 mL) and washed with water (100 mL) and 10% sodium bisulfite (100 mL). The organic layer was dried over magnesium sulfate, filtered, evaporated on a rotavap, and dried on the high vacuum overnight to give a brown oil (14.4 g, 85%).

Example 13: Surfactant Properties of the Oligomeric Terpolymers

The solubility, critical micelle concentration (CMC), surface tension, cloud point at CMC, and the solubility in 5 M $CaCl_2$ for each of the compounds prepared in Examples 1 to 12, as well as those of the starting alcohol ethoxylate compounds, were determined using standard procedures. Table 1 presents the results.

TABLE 1

| Surfactant Parameters | | | | | |
|---|---|---|---|---|---|
| Sample | Solubility (mM) | CMC (mM) | Surface Tension at CMC (mN/m) | Cloud Point at 1 wt % (C. °) | Solubility in 5 Molar $CaCl_2$ at 1 wt. % Concentration |
| Example 1 | 0.0019 | — | — | Insoluble | |
| Example 2 | >1000 | 0.041 | 32.2 | >75 | Soluble |
| Polyoxyethylene (4) lauryl ether | 0.20 | 0.018 | 31.6 | >75 | |
| Example 3 | 20 | 0.018 | 36.5 | 40 | Insoluble |
| Example 4 | 20 | 0.0069 | 38.1 | >75 | Soluble |
| Polyoxyethylene (20) cetyl ether | 0.10 | 0.0047 | 37.3 | 55 | |
| Example 7 | 100 | 0.0032 | 40.4 | >75 | |
| Example 8 | 50 | 0.0071 | 41.1 | >75 | Soluble |
| Polyoxyethylene (20) cetyl ether | 33 | 0.0028 | 43.8 | >75 | |
| Example 5 | 0.10 | 0.0047 | 41.0 | Insoluble | |
| Example 6 | 0.20 | 0.0069 | 50.0 | >75 | |
| Polyoxyethylene (10) stearyl ether | 0.30 | 0.0056 | 40.5 | 61 | |
| Example 9 | 50 | — | — | >75 | |
| Example 10 | 20 | 0.0042 | 37.9 | >75 | |
| Polyoxyethylene (20) stearyl ether | 20 | 0.0029 | 44.7 | >75 | |
| Example 11 | — | — | — | — | |
| Example 12 | 20 | — | — | >70 | |
| Polyoxyethylene (10) oleyl ether | 20 | — | — | 65 | |

Example 14: $M_n$ and PDI Data for Oligomeric Terpolymers

The oligomeric terpolymers prepared in Examples 1 to 12 were characterized in terms of number average molecular weight ($M_n$) and PDI (based on polystyrene standards) by gel permeation chromatography (GPC) with Tosoh EcoSEC instrument equipped with two TSKgel Super Multipore HZ-columns and an RI detector. The system was calibrated with standard polystyrenes with $M_n$ from 580 to 7.5×10(6) g/mol. The solution was eluted with THF at 40° C. at a flowing rate of 0.35 ml/min. Table 2 presents the results.

TABLE 2

$M_n$ and PDI Data

| Sample | $M_n$ | PDI ($M_w/M_n$) |
| --- | --- | --- |
| Example 1 | 710 | 1.13 |
| Example 2 | 580 | 1.13 |
| Example 3 | 1,100 | 1.10 |
| Example 4 | 960 | 1.10 |
| Example 7 | 1,600 | 1.06 |
| Example 8 | 1,200 | 1.13 |
| Example 5 | 1,200 | 1.10 |
| Example 6 | 980 | 1.09 |
| Example 9 | 1,600 | 1.06 |
| Example 10 | 1,300 | 1.10 |

Example 15: Laundry Test

Laundry formulations were formulated that comprised 10 wt % of a nonionic surfactant (e.g., oligomeric terpolymer, Igepal, etc.), 10 wt % of an anionic surfactant (e.g., SDBS), 0.2 wt % of sodium methyl cocoyl taurate, 0.2 wt % sodium diethylenetriamine penta(methylene phosphoric acid), 5 wt % sodium citrate, 0.8 wt % sodium chloride, 2 wt % sodium hydroxide, 0.3 wt % boric acid, 3% wt % propylene glycol, 0.1 wt % fluorescer, 0.4 wt % protease, 0.15 wt % mannanase, 0.4 wt % amylase, 0.2 wt % polyvinylpyrroldinone, 0.2 wt % polyvinylpyridine oxide, with water to balance.

The laundry formulations were tested on a series of different types of stains on cotton swatches and polyester-cotton (PE/C) swatches. Fabrics were purchased from Testfabrics Inc. The laundry formulation presented above was diluted at a 3 g in 1 liter tap water ratio and run through a 20 min wash plus a 5 min rinse cycle at 30° C. Reflectance was measured at a wavelength of 460 nm using an optoelectric colorimeter using a modification of testing procedure D4265-98 (Reapproved 2007). The changes in reflectance of a formulation comprising the terpolymer prepared in Example 2 relative to a control formulation comprising Igepal® CO 630 are presented in Table 3. A positive value indicates better cleaning efficiency as compared to the control formulation. On the average, the formulation comprising the sulfoxide oligomeric terpolymer had no changes in reflectance relative to the control formulation.

TABLE 3

Change in Reflectance Normalized to Control Formulation with Igepal ® CO 630 as the Nonionic Surfactant

| Type of Stain | Test formulation relative to the control formulation |
| --- | --- |
| Blood/milk/ink on cotton | 69% ± 20% |
| Tea on cotton | 30% ± 57% |
| Coffee on cotton | −43% ± 12% |
| Grass on cotton | −5% ± 13% |
| Wine on cotton | −18% ± 3% |
| Lipstick on cotton | 36% ± 19% |
| Chocolate drink on cotton | −2% ± 10% |
| Blood/milk/ink on PE/C | 37% ± 19% |
| Tea on PE/C | 65% ± 67% |
| Coffee on PE/C | −47% ± 11% |
| Grass on PE/C | −2% ± 7% |

TABLE 3-continued

Change in Reflectance Normalized to Control Formulation with Igepal ® CO 630 as the Nonionic Surfactant

| Type of Stain | Test formulation relative to the control formulation |
| --- | --- |
| Wine on PE/C | −5% ± 4% |
| Lipstick on PE/C | −2% ± 20% |
| Chocolate drink on PE/C | −12% ± 8% |
| Average | 7% ± 27% |

Example 16: Toxicology Studies

The potential toxicity of the oligomeric terpolymers was examined by evaluating the toxicity of compound prepared in similar manner to Example 2 in three standard bioassays. The bioassays were a fresh water algae growth inhibition test, a *Daphnia* acute immobilization test, and a fresh water fish acute toxicity test.

The fresh water algae growth inhibition test was conducted according to OECD guideline 210. Briefly, exponentially growing fresh water algae (i.e., *Pseudokirchneriella subcapitata*) were exposed to several concentrations of the test substance in batch cultures over a period of 72 hours. The cultures were allowed unrestricted exponential growth under nutrient-sufficient conditions and continuous fluorescent illumination. Three replicates at each test concentration were used. Growth was monitored over time and compared to the average growth of control cultures (with no test substances). Growth and growth inhibition are quantified from measurements of the algal biomass as a function of time. These data were used to calculate EC50, which is the concentration of the test substance that results in a 50 percent reduction in growth relative to the control. At 72 hr, the test compound had an EC50 of 640 µg/L, with 95% confidence intervals of 600 and 690 µg/L.

The *Daphnia* acute immobilization test was performed according to OECD guideline 202. Briefly, young daphnids, ages less than 24 hours at the start of the test, were exposed to the test substance at a range of concentrations for a period of 48 hours. Generally, at least 20 animals, preferably divided into four groups of five animals each, were tested for each test concentration and for the controls (i.e., no test substance). The *Daphnia* were not fed during the test. At least 2 mL of test solution were provided for each animal. Temperatures were held between 18 and 22° C., and for each single test the temperature was within ±1° C. Immobilization was recorded at 24 hours and 48 hours, and compared to control values. Those animals that could not swim within 15 seconds after gentle agitation of the test container were considered to be immobile. The results are used to calculate the EC50 (the concentration at which 50% of the animals were immobilized) at 48 hours. The EC50 of the test compound at 48 hr was 1.4 mg/L, with 95% confidence intervals of 1.1 and 1.7 mg/L.

The fresh water fish acute toxicity test was conducted according to OECD guideline 203. For this test, fresh water fish (i.e., fathead minnows, *Pimephales promelas*) were exposed to a series of concentrations of the test substance for a period of 96 hours. At least seven fishes were used at each test concentration and in the controls. Mortalities were recorded at 24, 48, 72, and 96 hours. Fish were considered dead if there was no visible movement (e.g. gill movements) and if touching of the caudal peduncle produced no reaction. The mortality counts were used to determine LC50, the concentration that killed 50% of the fish. The test compound had a LC50 of 5.5 mg/L ppm at 96 hr, with 95% confidence intervals of 3.7 and 8.0 mg/L.

Example 17: Biodegradation

The biodegradability of a compound prepared in a similar manner to Example 2 was determined using OECD Method 301B ($CO_2$ evolution test). For this, activated sludge was inoculated with test substance, and the mixture was incubated for 28 days under positive pressure using $CO_2$-free air in order to provide oxygen for the microbes and to capture evolved carbon dioxide. The temperature ranged from about 20-22° C. The test substance showed considerable biodegradation (55.95%) during the test period.

Example 18: Preparation of Amide Terpolymers

Oligomeric amide terpolymers may be prepared by first protecting the alcohol group of 2-hydroxy-4-(methylthio) butanoic acid (~1 eq.) by contacting the compound in a solvent such as dichloromethane (0.34 M) at a temperature of 0-5° C. and in the presence of a trialkyl amine base such as triethylamine (~2 eq.) with acetyl chloride (~1.1 eq.) and then allowing the reaction to warm to room temperature overnight with stirring. The protected product may be isolated from the reaction by washing with appropriate amounts of 1N HCl and/or brine followed by drying over magnesium sulfate and evaporation on a rotovap. The protected compound (~1 eq.) in an appropriate solvent such as dichloromethane (0.32 M) at 0-5° C. may be activated by contact with an activating agent, such as thionyl chloride (~5 eq.) and then allowing the reaction to warm to room temperature overnight with stirring, followed by rotary evaporation and drying under high vacuum. The activated compound (~1 eq.) in a solvent such as dichloromethane (0.32 M) at 0-5° C. and in the presence of a trialkyl amine base such as triethylamine (~2 eq.) may be contacted with an alkyl amine ethoxylate (~1 eq.) and the reaction allowed to warm to room temperature overnight to form an amide compound. The amide compound may be isolated from the reaction by washing with appropriate amounts of 1N HCl, sodium bicarbonate, and/or brine followed by drying over magnesium sulfate and rotary evaporation. The sulfur of the amide compound may be converted to a sulfoxide by contacting it in a solvent such as ethyl acetate or dichloromethane (1.3 M) at 0-5° C. with an oxidizing agent, such as 30% hydrogen peroxide (~1.3 eq.) added dropwise, and when the exotherm from the reaction has subsided, allowing the reaction to warm to room temperature overnight. The excess oxidizing agent may be quenched by addition of the appropriate amount of 10% sodium sulfite solution and the product isolated by separating the organic layer, washing it with 5% sodium bicarbonate and water and evaporating on the rotovap. The protecting acetyl group (~1 eq.) may be removed in a solution of methanol (0.25 M) by contact with a base (~1.5 eq.), such as 1M sodium hydroxide and stirring overnight. The product of the reaction may be isolated by evaporating to a small volume and addition of an organic solvent such as ethyl acetate or dichlormethane (~0.2 M), washing with 1N HCl, drying over magnesium sulfate and evaporating to give the desired product. The reaction scheme is diagrammed below:

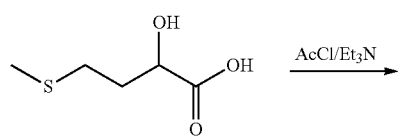

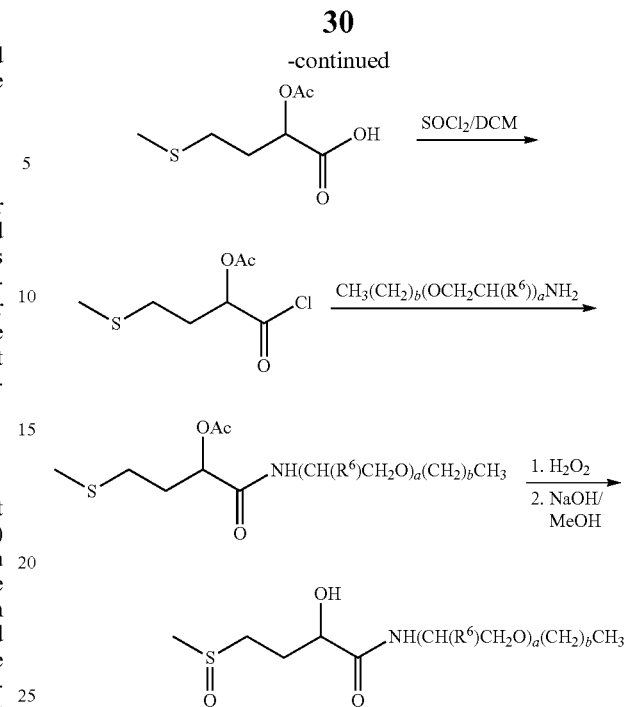

wherein $R^6$ is as defined above, a is an integer of 1 or greater, and b is an integer of 2 or greater.

Example 19: Alternate Preparation of Amide Terpolymers

Oligomeric amide terpolymers may be prepared by contacting methyl 2-hydroxy-4-(methylthio)butyrate (~1 eq.) with an alkyl amine ethoxylate (~1 eq.) and heating at 100° C. overnight to form an amide compound. The sulfur may be converted to a sulfoxide in a solvent such as dichloromethane by contact with an oxidizing agent, such as hydrogen peroxide in a similar manner as described in Example 18. The reaction scheme is diagrammed below:

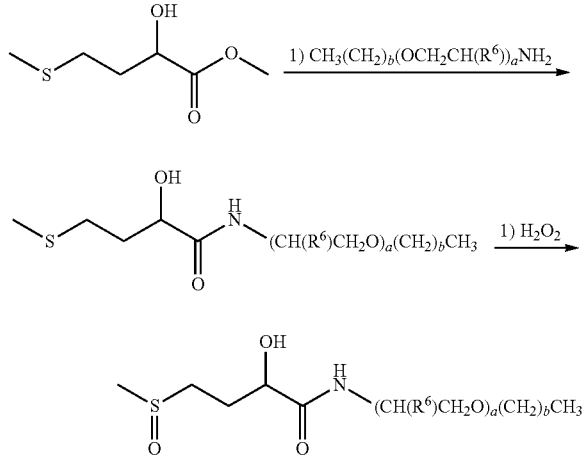

wherein $R^6$, a, and b are as defined above.

What is claimed is:

1. A compound of Formula (I):

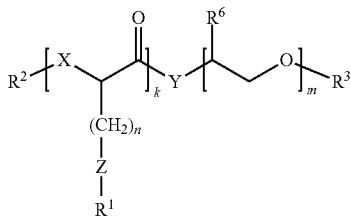

wherein:
- $R^1$ is hydrocarbyl or substituted hydrocarbyl;
- $R^2$ is hydrogen, hydrocarbyl, or substituted hydrocarbyl;
- $R^3$ is alkyl or alkenyl having 3 or more carbon atoms;
- $R^6$ is hydrogen or alkyl;
- X is O;
- Y is O or NH;
- Z is sulfur, sulfoxide, sulfone, or selenium;
- k is an integer from 1 to 500;
- n is an integer from 1 to 20; and
- m is an integer from 1 to 500.

2. The compound of claim 1, wherein $R^1$ is $C_1$ to $C_{10}$ alkyl, $R^2$ is hydrogen or $C_1$ to $C_{10}$ alkyl, $R^3$ is $C_3$ to $C_{200}$ alkyl or alkenyl, $R^6$ is hydrogen or $C_1$ to $C_{10}$ alkyl, n is from 1 to 10, k is from 1 to 300, and m is from 1 to 300.

3. The compound of claim 1, wherein $R^1$ is methyl; $R^2$ is hydrogen; $R^3$ is $C_6$ to $C_{30}$ alkyl or alkenyl, $R^6$ is hydrogen; Z is sulfur or sulfoxide; n is 2; k is from 1 to 10, and m is from 1 to 30.

4. The compound of claim 1, wherein the compound has a critical micelle concentration (CMC) of less than about 1 mM in water at 25° C. and atmospheric pressure.

5. The compound of claim 1, wherein the compound is part of a composition further comprising at least one agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a preservative, a coloring agent, a fragrance agent, or combinations thereof.

6. A composition comprising the compound of claim 1 and at least one additional compound of Formula (I), wherein each compound of Formula (I) differs and has the following structure:

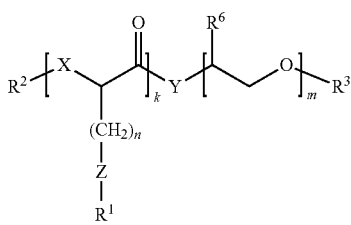

wherein:
- $R^1$ is hydrocarbyl or substituted hydrocarbyl;
- $R^2$ is hydrogen, hydrocarbyl, or substituted hydrocarbyl;
- $R^3$ is alkyl or alkenyl having 3 or more carbon atoms;
- $R^6$ is hydrogen or alkyl;
- X and Y independently are O or NH;
- Z is sulfur, sulfoxide, sulfone, or selenium;
- k is an integer from 1 to 500;
- n is an integer from 1 to 20; and
- m is an integer from 1 to 500.

7. The composition of claim 6, wherein $R^1$ is $C_1$ to $C_{10}$ alkyl, $R^2$ is hydrogen or $C_1$ to $C_{10}$ alkyl, $R^3$ is $C_3$ to $C_{200}$ alkyl or alkenyl, $R^6$ is hydrogen or $C_1$ to $C_{10}$ alkyl, n is from 1 to 10, k is from 1 to 300, and m is from 1 to 300.

8. The composition of claim 6, wherein $R^1$ is methyl; $R^2$ is hydrogen; $R^3$ is $C_6$ to $C_{30}$ alkyl or alkenyl, $R^6$ is hydrogen; Z is sulfur or sulfoxide; X is O; Y is O or NH; n is 2; k is from 1 to 10, and m is from 1 to 30.

9. The composition of claim 8, wherein the composition comprises at least a first set of compounds in which k is 1 and $R^3$ is $C_8$ to $C_{12}$ alkyl or alkenyl; and a second set of compounds in which k is 1 and $R^3$ is $C_{14}$ to $C_{18}$ alkyl or alkenyl.

10. The composition of claim 8, wherein the composition comprises at least a first set of compounds in which k is 1 and $R^3$ is $C_8$ to $C_{18}$ alkyl or alkenyl; a second set of compounds in which k is 2 and $R^3$ is $C_8$ to $C_{18}$ alkyl or alkenyl; and a third set of compounds in which k is 3 and $R^3$ is $C_8$ to $C_{18}$ alkyl or alkenyl.

11. The composition of claim 6, wherein the composition comprises at least a first set of compounds in which Z is sulfur; and a second set of compounds in Z is sulfoxide.

12. The composition of claim 6, wherein the composition has a critical micelle concentration (CMC) of less than about 0.3 mM in water at 25° C. and atmospheric pressure.

13. The composition of claim 6, further comprising at least one agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a preservative, a coloring agent, a fragrance agent, or combinations thereof.

14. The composition of claim 6, wherein the composition is used in commercial or residential laundry products, industrial or household cleaning products, floor polishing products, personal care or cosmetic products, textile processing, metal processing, agricultural applications, latex production, paper de-inking, crude oil drilling, or crude oil refining applications.

15. A method for cleaning an article, the process comprising contacting the article with a composition comprising at least one compound of Formula (I):

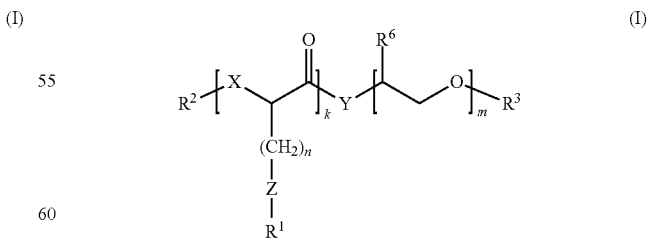

wherein:
- $R^1$ is hydrocarbyl or substituted hydrocarbyl;
- $R^2$ is hydrogen, hydrocarbyl, or substituted hydrocarbyl;
- $R^3$ is alkyl or alkenyl having 3 or more carbon atoms;

R⁶ is hydrogen or alkyl;

X and Y independently are O or NH;

Z is sulfur, sulfoxide, sulfone, or selenium;

k is an integer from 1 to 500;

n is an integer from 1 to 20; and m is an integer from 1 to 500.

16. The method of claim 15, wherein $R^1$ is $C_1$ to $C_{10}$ alkyl, $R^2$ is hydrogen or $C_1$ to $C_{10}$ alkyl, $R^3$ is $C_3$ to $C_{200}$ alkyl or alkenyl, $R^6$ is hydrogen or $C_1$ to $C_{10}$ alkyl, n is from 1 to 10, k is from 1 to 300, and m is from 1 to 300.

17. The method of claim 15, wherein $R^1$ is methyl; $R^2$ is hydrogen; $R^3$ is $C_6$ to $C_{30}$ alkyl or alkenyl; $R^6$ is hydrogen; Z is sulfur or sulfoxide; X is O; Y is O or NH; n is 2; k is from 1 to 10, and m is from 1 to 30.

18. The method of claim 17, wherein the composition comprises at least a first set of compounds in which k is 1 and $R^3$ is $C_8$ to $C_{12}$ alkyl or alkenyl; and a second set of compounds in which k is 1 and $R^3$ is $C_{14}$ to $C_{18}$ alkyl or alkenyl.

19. The method of claim 17, wherein the composition comprises at least a first set of compounds in which k is 1 and $R^3$ is $C_8$ to $C_{18}$ alkyl or alkenyl; a second set of compounds in which k is 2 and $R^3$ is $C_8$ to $C_{18}$ alkyl or alkenyl; and a third set of compounds in which k is 3 and $R^3$ is $C_8$ to $C_{18}$ alkyl or alkenyl.

20. The method of claim 15, wherein the article is an inanimate object chosen from laundry item, food or cookware item, kitchen or bathroom appliance, counter, wall, floor, and other surface, or an animate object or a part of an animate object chosen from hair, hands, face, or other body parts.

21. The method of claim 15, wherein the composition further comprises at least one agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a preservative, a coloring agent, a fragrance agent, or combinations thereof.

22. A polymer comprising:

a) at least one subunit A having the following structure:

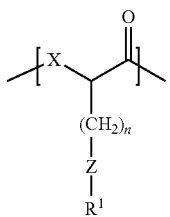

b) at least one subunit B having the following structure:

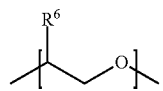

and c) at least one subunit C, optionally unsaturated, having the following structure:

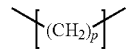

wherein:

$R^1$ is alkyl;

$R^6$ is hydrogen or alkyl;

X is O or NH;

Z is sulfur, sulfoxide, sulfone, or selenium;

n is an integer from 1 to 20; and p is an integer from 3 to 500;

wherein the polymer is a block polymer in which the subunits are arranged A-B-C, and the polymer comprises up to about 500 repeats of each subunit.

23. The polymer of claim 22, wherein $R^1$ is $C_1$ to $C_{10}$ alkyl, $R^6$ is hydrogen or $C_1$ to $C_{10}$ alkyl, n is from 1 to 10, and p is from 3 to 200.

24. The polymer of claim 23, wherein $R^1$ is methyl; $R^6$ is hydrogen or methyl, X is oxygen, Z is sulfur or sulfoxide, n is 2, and p is from 6 to 30.

25. The polymer of claim 22, further comprising at least one linker, the linker comprising at least one atom.

26. The polymer of claim 22, wherein the composition has a critical micelle concentration (CMC) of less than about 1 mM in water at 25° C. and atmospheric pressure.

27. The polymer of claim 22, wherein the polymer is part of a composition further comprising at least one agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a preservative, a coloring agent, a fragrance agent, or combinations thereof.

* * * * *